United States Patent

Delfort et al.

[11] Patent Number: 5,854,184
[45] Date of Patent: Dec. 29, 1998

[54] COLLOIDAL PRODUCTS, THEIR PREPARATION AND THEIR USES

[75] Inventors: Burno Delfort, Paris; Thierry Lacome, Rueil Malmaison; Maurice Born, Nantierra, all of France

[73] Assignee: Institut Francais du Petrole, France

[21] Appl. No.: 842,326

[22] Filed: Apr. 24, 1997

[30] Foreign Application Priority Data

Apr. 25, 1996 [FR] France .................... 96 05403

[51] Int. Cl.$^6$ .............................................. C10M 135/10
[52] U.S. Cl. ............................................ 508/405
[58] Field of Search ................... 508/391, 405

[56] References Cited

U.S. PATENT DOCUMENTS

| | | | |
|---|---|---|---|
| 2,786,029 | 3/1957 | Brugmann, Jr. ............... | 252/32.7 |
| 2,965,665 | 12/1960 | Gaertner et al. ............... | 508/485 |
| 3,718,589 | 2/1973 | Rogers et al. ............... | 508/391 |
| 4,541,940 | 9/1985 | Spence ............... | 252/33 |
| 4,824,584 | 4/1989 | Muir et al. ............... | 252/39 |
| 5,449,470 | 9/1995 | Cahoon et al. ............... | 508/391 |

FOREIGN PATENT DOCUMENTS

| | | |
|---|---|---|
| 0 438 942 | 7/1991 | European Pat. Off. . |
| 2101813 | 3/1972 | France . |
| 2616441 | 12/1988 | France . |
| 1444807 | 3/1969 | Germany . |

Primary Examiner—Jacqueline V. Howard
Attorney, Agent, or Firm—Millen, White, Zelano & Branigan, P.C.

[57] ABSTRACT

New overbased colloidal products that comprise a core of micellized alkali metal or alkaline-earth metal carbonate, surrounded by a ring of at least one surfactant compound that is selected from among the dihydrocarbyl-dithiophosphoryl-alkane-sulfonic acids, and their salts of alkali metals or alkaline-earth metals are described. They are derived from the carbonation of at least one oxide or hydroxide of an alkali metal or alkaline-earth metal that is carried out within an oily medium that contains hydrocarbon in the presence of at least one dihydrocarbyl-dithiophosphoryl-alkane-sulfonic acid that corresponds to general formula:

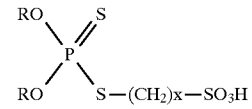

in which R represents a monovalent aliphatic, cycloaliphatic or aromatic radical that contains 1 to 30 carbon atoms and x has a value of 3 to 6, or an alkali metal or alkaline-earth metal salt of such an acid. These colloidal products can be used as detergent additives notably providing anti-wear and extreme-pressure properties in lubricants. Because of the presence in their molecule of dihydrocarbyl-dithiophosphoric groups, they also exhibit anti-oxidizing properties.

13 Claims, No Drawings

COLLOIDAL PRODUCTS, THEIR PREPARATION AND THEIR USES

BACKGROUND OF THE INVENTION

The invention relates to new overbased colloidal products, their preparation and their uses.

It relates more particularly to overbased colloidal products that exhibit detergent properties that can be used particularly as anti-wear and extreme-pressure additives in lubricating, mineral or synthetic oils, for example in motor oils, gear lubricant oils, hydraulic fluids or else oils for metal-working.

Overbased detergent additives have been known for a long time. Some of them and their preparation have been described in, for example, U.S. Pat. Nos. 2,865,956, 3,150,088, 3,537,996, 3,830,739, 3,865,737, 3,953,519, 3,966,621, 4,148,740 and 4,505,830, and in French Patent FR-B-2 101 813. These detergent additives are generally obtained by carbonation, for example, by carbon dioxide, an alkali metal or alkaline-earth metal hydroxide, with the carbonate formed being kept in colloidal suspension in the medium that contains hydrocarbon with a surfactant compound, which is generally selected from among the oil-soluble sulfonic acids and their salts.

SUMMARY OF THE INVENTION

New overbased colloidal products that belong to the class mentioned above, but in which the sulfonic acids are special compounds that contain sulfur and phosphorus, namely dihydrocarbyl-dithiophosphoryl-alkane-sulfonic acids or their salts, whose use imparts improved properties to the final colloidal products, have now been discovered.

The overbased colloidal products of the invention can be defined, in a general way, as comprising, kept under micellized form within an oily medium that contains hydrocarbon, a core of alkali metal or alkaline-earth metal carbonate that is surrounded by a ring of at least one surfactant compound that is selected from among the dihydrocarbyl-dithiophosphoryl-alkane-sulfonic acids that correspond to general formula:

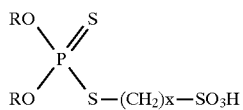

in which R represents a monovalent radical that contains hydrocarbon with 1 to 30 carbon atoms, which can be aliphatic, cycloaliphatic or aromatic and x has a value of 3 to 6, preferably 3 or 4, and the alkali metal or alkaline-earth metal salts of these acids.

As examples of such dihydrocarbyl-dithiophosphoryl-alkane-sulfonic acids that can be used for preparing the colloidal products of the invention, it is possible to cite more particularly those in which number x is 3: these are the dihydrocarbyl-dithiophosphoryl-3-propane-sulfonic acids; and those in which number x is equal to 4: these are the dihydrocarbyl-dithiophosphoryl-4-butane-sulfonic acids. Furthermore, the various dihydrocarbyl-dithiophosphoryl-alkane-sulfonic acids that can be obtained by varying radical R can be cited. Thus, among various radicals R, more particularly dodecyl, didodecyl, etc., can be cited. The alkali metal or alkaline-earth metal salts of the dihydrocarbyl-dithiophosphoryl-alkane-sulfonic acids that are defined above are also considered.

The preparation of the overbased colloidal products of the invention can be carried out, for example, by the method that is described below.

In a first stage (a), a suitable dihydrocarbyl-dithiophosphoryl-alkane-sulfonic acid or acid salt at a concentration that can range from, for example, 5 to 100% by mass relative to said medium, as well as an oxide or a hydroxide of an alkali metal or alkaline-earth metal, used, for example, at a ratio of 20 to 200% by mass relative to said dihydrocarbyl-dithiophosphoryl-alkane-sulfonic acid or to said salt, are introduced into an oily medium that contains hydrocarbon, for example into a mineral or synthetic lubricating oil. At least one aliphatic, cycloaliphatic or aromatic solvent that contains hydrocarbon, such as toluene, is also introduced into the medium, for example at ratios that make it possible to operate at a reagent concentration of 2 to 70% by mass in the reaction medium, and, as a promoter, at least one oxidized organic liquid such as an alcohol, for example, methanol, for example at a ratio of 5 to 40% by volume relative to said solvent that contains hydrocarbon.

In a second stage (b), the carbonation of the alkali metal or alkaline-earth oxide or hydroxide is carried out by introducing into the medium, while being stirred continuously, carbon dioxide ($CO_2$) at a ratio of 2 to 100 mol % relative to said alkali metal or alkaline-earth oxide or hydroxide. This introduction can be made at, for example, ambient temperature; it can last from, for example, 5 minutes to 3 hours. During the time of introduction of the carbon dioxide, it is preferred to keep the temperature at a value that is below about 45° C.

After the end of the reaction, in a third stage (c), the medium is filtered to remove from it possible solid particles of oxide or hydroxide which would not have reacted during carbonation, and the reaction medium is separated by, for example, decantation, with the oxidized organic liquid (for example alcohol) used as promoter. After the aliphatic, cycloaliphatic or aromatic solvent that contains hydrocarbon (for example, toluene) is evaporated, the desired colloidal product is obtained in the form of a clear suspension in the initial oily medium that contains hydrocarbon.

In stage (a), as an oxide or hydroxide of an alkali metal or alkaline-earth metal, it is possible to use, for example, those of sodium, potassium, magnesium, calcium or barium.

The products of the invention, for example, such as those obtained by the method that is described above, result in the form of stable colloidal suspensions in the oily medium that contains hydrocarbon in which they were formed; they contain proportions of alkali metal or alkaline-earth metal that can range from, for example, 3 to 30% by mass and exhibit a basicity rate (or alkaline reserve), represented by a base number (abbreviated BN), that can range from, for example, 50 to 550 mg of potash per gram of product, excluding diluting oil. They generally have a sulfur content of 2 to 10% by mass and a phosphorus content of 0.3 to 7% by mass. They have very good solubility in lubricating, mineral or synthetic oils.

The overbased colloidal products with detergent action according to the invention can be used as additives in lubricating, mineral or synthetic oils, for example in motor oils, gear lubricant oils, hydraulic fluids or else metal-working oils. They are generally incorporated in lubricating oils at ratios that can range from, for example, 0.5 to 20%, and more particularly 2 to 10% by mass of active ingredient (i.e., excluding diluting oil).

In addition to the anti-wear and extreme-pressure properties that they impart to the lubricating, mineral or synthetic oils, in which they are incorporated, the overbased, colloidal products according to the invention offer the important advantage of also imparting to them anti-oxidizing properties because of the presence in their molecule of dihydrocarbyl-dithiophosphoric groups.

The dihydrocarbyl-dithiophosphoryl-alkane-sulfonic acids that are used as surfactants to prepare the colloidal products of the invention can be prepared according to the methods that are described below.

If the corresponding dihydrocarbyl-dithiophosphoric acid is available, it can be reacted directly on a sultone of the general formula:

in which number x assumes a value of 3 to 6, preferably 3 or 4, depending on the dihydrocarbyl-dithiophosphoryl-alkane-sulfonic acid that is targeted for synthesis. Thus, to prepare a dihydrocarbyl-dithiophosphoryl-3-propane-sulfonic acid, propane-sultone will be used; and to prepare a dihydrocarbyl-dithiophosphoryl-4-butane-sulfonic acid, butane-sultone will be used.

The initial dihydrocarbyl-dithiophosphoric acid can be prepared by a process that is known in the art, by reacting an alcohol or a phenol of formula ROH, where R is defined as above with tetraphosphorus decasulfide $P_4S_{10}$. The synthesis of the dihydrocarbyl-dithiophosphoric acids and their salts has already been described in the prior art in many documents. For example, U.S. Pat. Nos. 2,364,283, 2,364,284, 2,365,938, 2,410,650, 2,438,876 and 3,190,833 can be cited. Thus, it is possible to react tetraphosphorus decasulfide with an alcohol or a phenol within an organic, for example chlorinated, solvent. The solvent is heated under reflux until the hydrogen sulfide that is formed is completely eliminated.

The reaction of the dihydrocarbyl-dithiophosphoric acid with the sultone can be carried out within at least one organic polar solvent such as acetonitrile, optionally mixed with a small proportion of methanol, by, for example, refluxing the solvent. The solvent(s) is (are) cooled, then eliminated to obtain the desired dihydrocarbyl-dithiophosphoryl-alkane-sulfonic acid.

It is also possible to synthesize the dihydrocarbyl-dithiophosphoryl-alkane-sulfonic acids that are used in the invention from the corresponding dihydrocarbyl-dithiophosphoric acids in the following way.

The dihydrocarbyl-dithiophosphoric acid is neutralized by a hydroxide of an alkaline metal, for example, potash, in alcoholic medium, and the alcohol is eliminated. A salt, generally potassium, of the dihydrocarbyl-dithiophosphoric acid is thus isolated. The isolated dihydrocarbyl-dithiophosphoric acid salt is put into solution in an organic polar solvent or a mixture of organic polar solvents. In this connection, it is possible to use acetonitrile, optionally mixed with a small proportion of methanol. It is then caused to react with the suitable sultone. After reaction, for example, under solvent reflux, it is possible to separate, after cooling and elimination of the solvent, by for example evaporation under reduced pressure, the potassium salt of dihydrocarbyl-dithiophosphoryl-alkane-sulfonic acid. The salt that is obtained, after purification, is transformed into the corresponding sulfonic acid, by reaction with a strong acid, such as hydrochloric acid or sulfuric acid, within an organic, for example, a chlorinated, solvent. After the solvent is eliminated, for example, by evaporation, the desired dihydrocarbyl-dithiophosphoryl-alkane-sulfonic acid is obtained.

The alkali metal or alkaline-earth metal salts of the dihydrocarbyl-dithiophosphoryl-alkane-sulfonic acids can be prepared from the dihydrocarbyl-dithiophosphoryl-alkane-sulfonic acids themselves, as described below.

The dihydrocarbyl-dithiophosphoryl-alkane-sulfonic acid is caused to react with the suitable metallic hydroxide, generally within a solvent that contains hydrocarbon, such as, for example, toluene to which can be added, in a small proportion, an organic polar solvent, such as, for example, methanol. The salt that is obtained is then isolated by separation of excess hydroxide (in the case of a hydroxide suspension) and elimination of the solvent, for example by evaporation. The desired salt is isolated in solid form, generally with a good yield.

Furthermore, as already mentioned above, the alkaline metal salts of the dihydrocarbyl-dithiophosphoryl-alkane-sulfonicacids, in particular those of potassium, can be obtained intermediately in the preparation of the acids themselves.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding French application 96/05403, are hereby incorporated by reference.

In Example 1, the preparation of the dihydrocarbyl-dithiophosphoryl-alkane-sulfonic acid that will be used in Example 2 is described. Example 3 is given as a comparison. In Example 4, the performance levels of the products of Examples 2 and 3 are evaluated.

EXAMPLE 1

Synthesis of (O, O'-didodecyl-dithiophosphoryl)-4-butane-sulfonic acid of formula: $(C_{12}H_{25}-O)_2-P(S)-S-CH_2-CH_2-CH_2-CH_2-SO_3H$.

In a reactor that contains a solution of 16.8 g (0.09 mol) of n-dodecanol in 60 ml of chloroform, 5.0 g (0.0113 mol) of tetraphosphorus decasulfide is introduced within 10 minutes at 40° C. The medium is caused to reflux for 10 hours, then after filtration, the chloroform is evaporated. The acid that is formed is neutralized by a suitable amount of alcoholic potash, then the solvent is evaporated. The medium is then dissolved in 60 ml of an acetonitrile-methanol (90/10) mixture. A solution of 1.5 g (0.011 mol) of butane-sultone is then introduced drop by drop at 40° C. into 20 ml of acetonitrile. The mixture is brought to the reflux temperature for 2 hours, then the mixture is cooled and concentrated under reduced pressure. The salt that is obtained is purified by precipitation in cyclohexane, filtered then dried. The potassium sulfonate is then dissolved in 80 ml of chloroform, and then acidified. After the chloroform is evaporated, 16.5 g of a clear product is collected, whose characteristics are as follows:

Phosphorus content: 5.0% by mass (theoretical value: 5.15%)

Sulfur content: 7.9% by mass (theoretical value: 8.0%)

Acidity: 1.6 milliequivalents of acid/g (theoretical value: 1.66 meq/g)

NMR of phosphorus 31: single signal at 95.6 ppm.

EXAMPLE 2

In a reactor that is equipped with a stirring mechanism, a system for introducing gas and a condenser, 15.0 g (0.025 mol) of (O,O'-didodecyl-dithio-phosphoryl)-3-butane-sulfonic acid that is prepared as described in Example 1, 15.0 g of mineral oil 130 Neutral, 15.5 g (0.21 mol) of lime $Ca(OH)_2$, 60 ml of toluene and 15 ml of methanol are introduced. 6.6 g (0.15 mol) of carbon dioxide is then introduced while being stirred and at ambient temperature in about 30 minutes.

For the entire duration of the introduction, the temperature is kept below 35° C. After the medium is filtered, the alcoholic phase is eliminated by decantation, then after evaporation of the solvent, 38.0 g of a perfectly clear liquid product is obtained, whose characteristics are as follows:

Calcium content: 15.2% by mass

Phosphorus content: 1.6% by mass

Sulfur content: 5.3% by mass

Alkalinity reserve (BN): 385 mg of KOH/g.

The dialysis of the product in n-heptane through a latex membrane makes it possible to determine the amount of colloidal material (surfactant plus "core" of the calcium carbonate), as well as the amount of diluting oil:

Colloidal fraction: 68% by mass

Oil: 32% by mass

EXAMPLE 3 (FOR COMPARISON)

In a reactor that is equipped with a stirring mechanism, a system for introducing gas and a condenser, 15.0 g of a standard alkyl-aryl-sulfonic acid that is free of any group that contains phosphosulfur and average molecular weight equivalent to 700, 15.0 g of mineral oil 130 Neutral, 15.5 g (0.21 mol) of lime $Ca(OH)_2$, 80 ml of toluene and 35 ml of methanol are introduced. 8.0 g (0.18 mol) of carbon dioxide is then introduced while being stirred and at ambient temperature in about 30 minutes. For the entire duration of the introduction, the temperature is kept below 35° C. After the medium is filtered, the alcoholic phase is eliminated by decantation, then after evaporation of the solvent, 39.5 g of a clear liquid product is obtained, whose characteristics are as follows:

Calcium content: 14.0% by mass

Phosphorus content: 0.0% by mass

Sulfur content: 1.3% by mass

Alkalinity reserve (BN): 405 mg of KOH/g.

The dialysis of the product in n-heptane through a latex membrane makes it possible to determine the amount of colloidal material (surfactant plus "core" of calcium carbonate) as well as the amount of diluting oil:

Colloidal fraction: 58% by mass

Oil: 42% by mass.

EXAMPLE 4

Evaluation of anti-wear and extreme-pressure performance levels.

The product of the invention that is prepared as described in Example 2 above is characterized for its antiwear and extreme-pressure properties in a mineral oil 130 Neutral Solvent at a concentration that makes it possible to adjust the content of active ingredient (colloidal fraction) in the oil at 7.5% by mass. The characterization is carried out with a four-ball machine according to the ASTM D-2783 test. The results are summarized in Table 1 below. Also present by way of comparison are the results that are obtained with the standard colloidal product of calcium carbonate, obtained as described in Example 3 from a standard alkyl-aryl-sulfonic surfactant that is free of dialkyldithiophosphoric groups. The examination of the results confirms the better anti-wear and extreme-pressure performance levels of the product of the invention whose surfactant chain carries groups that contain phosphosulfur.

TABLE 1

| Product of the Example | Concentration of Active Ingredient/Oil (% by Mass) | Solder Batch (daN) | Diameter of Imprint after 1 Hour under 40 daN (mm) | Diameter of Imprint after 1 Hour under 80 daN (mm) |
|---|---|---|---|---|
| 2 | 7.5 | 250 | 0.34 | 0.44 |
| 3 | 7.5 | 180 | 0.41 | 1.95 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

In the specification and in the following claims, the expression "surrounded by a ring of at least one surfactant compound" means that the core is at least partially and preferably completely surrounded by a layer or shell of the surfactant.

What is claimed:

1. An overbased colloidal product comprising in a micellized form within an oily hydrocarbon-containing medium, a core of alkali metal or alkaline-earth metal carbonate, surrounded by a ring of at least one dihydrocarbyl-dithiophosphoryl-alkane-sulfonic acid surfactant of the formula:

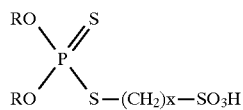

in which R represents a monovalent radical that contains hydrocarbon with 1 to 30 carbon atoms which can be aliphatic, cycloaliphatic or aromatic and x has a value of 3 to 6, and their alkali metal or alkaline-earth metal salts.

2. A colloidal product according to claim 1, derived from the carbonation of at least one oxide or hydroxide of an alkali metal or alkaline-earth metal in an oily medium that contains hydrocarbon in the presence of said dihydrocarbyl-dithiophosphoryl-alkane-sulfonic acid or of a salt thereof.

3. A colloidal product according to claim 1, prepared by the following stages:
   a) introducing at least one dihydrocarbyl-dithiophosphoryl-alkane-sulfonic acid or at least one dihydrocarbyl-dithiophosphoryl-alkane-sulfonic acid salt or a mixture thereof and at least one oxide or a hydroxide of an alkali metal or alkaline-earth metal into an oily medium that contains hydrocarbon in the presence of at least one aliphatic, cycloaliphatic or aromatic solvent that contains hydrocarbon and, as a promoter, at least one oxygenated polar organic liquid;
   b) introducing $CO_2$ into the resultant medium while being stirred continuously to provide carbonation;

c) after the end of the carbonation reaction, filtering the medium to remove any residual particles of oxide or hydroxide of an alkali metal or alkaline-earth metal which would not have reacted during said carbonation, and separating said oxidized organic liquid by decantation; and d) evaporating said aliphatic, cycloaliphatic or aromatic solvent that contains hydrocarbon to obtain the desired colloidal product in the form of a clear suspension in said initial oily medium that contains hydrocarbon.

4. A colloidal product according to claim 3, wherein in its preparation, in stage (a), said oily medium that contains hydrocarbon is a mineral or synthetic oil; the dihydrocarbyl-dithiophosphoryl-alkane-sulfonic acid or acid salt is used at a concentration ranging from 5 to 100% by mass relative to said oily medium that contains hydrocarbon; the oxide or hydroxide of an alkali metal or alkaline-earth metal is used at a ratio of 20 to 200% by mass relative to said dihydrocarbyl-dithiophosphoryl-alkane-sulfonic acid or acid salt; the aliphatic, cycloaliphatic or aromatic solvent that contains hydrocarbon is used at a ratio that makes it possible to operate at a concentration of reagents of 2 to 70% by mass; and the polar organic liquid that is used as a promoter is used at a ratio of 5 to 40% by volume relative to said solvent that contains hydrocarbon; and in stage (b), carbonation is carried out at a temperature ranging from ambient temperature up to a value of about 45° C.

5. A colloidal product according to claim 1, wherein in the formula of the dihydrocarbyl-dithiophosphoryl-alkane-sulfonic acid or acid salt, x has a value of 3 or 4.

6. A colloidal product according to claim 3, wherein in stage (a), an oxide or a hydroxide of sodium, potassium, magnesium, calcium or barium is used.

7. A colloidal product according to claim 1, in the form of a colloidal suspension that is stable in a medium that contains hydrocarbon, containing a proportion of alkali metal or alkaline-earth metal of 3 to 30% by mass; exhibiting a basicity of 50 to 550 mg of potash per gram of product, excluding diluting oil, a sulfur content of 2 to 10% by mass and a phosphorus content of 0.3 to 7% by mass.

8. A lubricating composition with improved anti-wear and extreme-pressure properties, comprising a major proportion of lubricating, mineral or synthetic oil, and a sufficient proportion of at least one colloidal product according to claim 1 to provide improved anti-wear and extreme pressure properties.

9. A lubricating composition according to claim 8, wherein said colloidal product is present at a ratio of 0.5 to 20% by mass.

10. A lubricating composition with improved anti-wear and extreme-pressure properties, comprising a major proportion of lubricating, mineral or synthetic oil, and a sufficient proportion of at least one colloidal product according to claim 5 to provide improved anti-wear and extreme pressure properties.

11. A lubricating composition according to claim 10, wherein said colloidal product is present at a ratio of 0.5 to 20% by mass.

12. A lubricating composition with improved anti-wear and extreme-pressure properties, comprising a major proportion of lubricating, mineral or synthetic oil, and a sufficient proportion of at least one colloidal product according to claim 7 to provide improved anti-wear and extreme pressure properties.

13. A lubricating composition according to claim 12, wherein said colloidal product is present at a ratio of 0.5 to 20% by mass.

* * * * *